United States Patent
Olive et al.

(10) Patent No.: US 9,243,052 B2
(45) Date of Patent: Jan. 26, 2016

(54) METHOD FOR TREATING AND DIAGNOSING HEMATOLOGIC MALIGNANCIES

(76) Inventors: Daniel Olive, Marseilles (FR); Luc Xerri, Marseilles (FR); Alemseged Truhneh, Sudbury, MA (US)

( * ) Notice: Subject to any disclaimer, the term of this patent is extended or adjusted under 35 U.S.C. 154(b) by 1359 days.

(21) Appl. No.: 12/673,721

(22) PCT Filed: Aug. 14, 2008

(86) PCT No.: PCT/EP2008/060699
§ 371 (c)(1),
(2), (4) Date: Mar. 14, 2011

(87) PCT Pub. No.: WO2009/024531
PCT Pub. Date: Feb. 26, 2009

(65) Prior Publication Data
US 2011/0177088 A1    Jul. 21, 2011

(30) Foreign Application Priority Data
Aug. 17, 2007 (EP) ..................... 07301312

(51) Int. Cl.
*A61K 39/395* (2006.01)
*C07K 14/705* (2006.01)
*C07K 14/47* (2006.01)
*C07K 16/28* (2006.01)
*G01N 33/574* (2006.01)

(52) U.S. Cl.
CPC ....... *C07K 14/70521* (2013.01); *C07K 14/4747* (2013.01); *C07K 16/2818* (2013.01); *C07K 16/2827* (2013.01); *G01N 33/57426* (2013.01)

(58) Field of Classification Search
USPC ............................ 424/144.1, 141.1; 530/350
See application file for complete search history.

(56) References Cited

FOREIGN PATENT DOCUMENTS

WO    2006/121168    11/2006

OTHER PUBLICATIONS

Gura (Science, 1997, 278:1041-1042).*
Kaiser (Science, 2006, 313: 1370).*
Busken, C et al. (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Greaves et al. (Blood, published online Sep. 4, 2013, p. 1-23).*
Nielsen et al. (Cellular Immunology, 2005, 235: 109-116).*
Taber's Cyclopedic Medical Dictionary (1985, F.A. Davis Company, Philadelphia, p. 274).*
Okazaki et al., International Immunology, 19(7):813-824 (2007).
Waldmann, Annu. Rev. Med., 57:65-81 (2006).

* cited by examiner

*Primary Examiner* — Yan Xiao
(74) *Attorney, Agent, or Firm* — McAndrews Held & Malloy, Ltd.

(57) ABSTRACT

The invention relates to methods for treating and diagnosing hematologic malignancies, Chronic lymphocytic leukemia and Small Lymphocytic Lymphoma in particular, using PD-1 ligands (PD-L1, PD-L2, or anti-PD-1 antibodies).

1 Claim, 1 Drawing Sheet

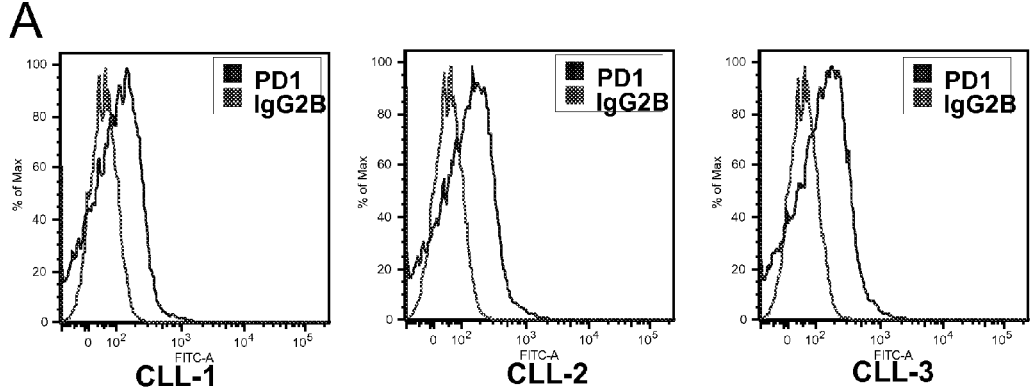
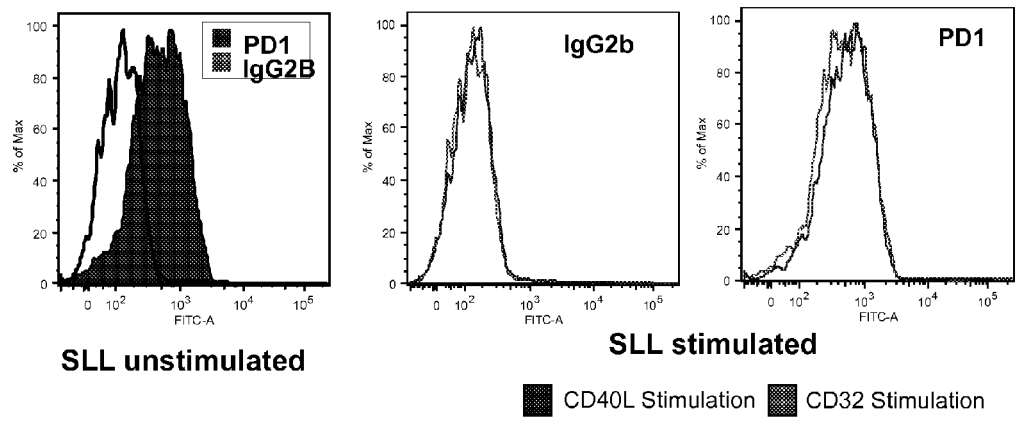
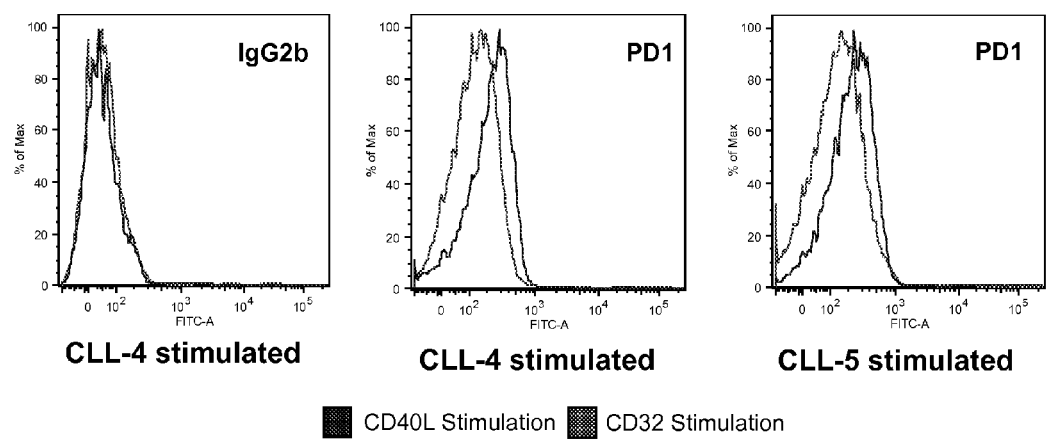

METHOD FOR TREATING AND DIAGNOSING HEMATOLOGIC MALIGNANCIES

The present application is filed pursuant to 35 U.S.C. 371 as a U.S. National Phase application of International Patent Application No. PCT/EP08/60699, which was filed Aug. 14, 2008, claiming the benefit of priority to European Patent Application No. 07301312.0, which was filed on Aug. 17, 2007. The entire text of the aforementioned applications is incorporated herein by reference in its entirety.

FIELD OF THE INVENTION

The present invention relates to methods for treating and diagnosing hematologic malignancies, Chronic lymphocytic leukemia (CLL) and Small Lymphocytic Lymphoma (SLL) in particular.

BACKGROUND OF THE INVENTION

Hematologic Malignancies

With respect to pathological conditions which involve the immune system, the diversity in the lineages and differentiation stages of hematopoietic cells results in a large number of distinct and heterogeneous tumors generally referred to as hematologic malignancies. Thus, hematologic malignancies or hematologic neoplasia affect cells and tissues of the immune and hematopoietic system, including blood, bone marrow and lymph nodes. Hematologic malignancies include both leukemias and lymphomas.

The term leukemia has generally been used to define hematologic malignancies of the blood or bone marrow characterized by abnormal proliferation of leukocytes. The principal subtypes of leukemia are identified on the basis of malignancy involving lymphoid (e.g. T or B lymphocytic lineage) or myeloid (e.g. granulocytic, erythroid or megakaryocytic lineage) cells, and whether the disease is acute or chronic in onset (Freireich, E. J. et al., 1991).

The term lymphoma covers a heterogeneous group of neoplasms of lymphoid tissue. Lymphomas are broadly categorized under Hodgkin lymphoma, and T-cell (T-NHL) and B-cell (B-NHL) non-Hodgkin lymphomas. A World Health Organization (WHO) classification has recently been published and diagnostic guidelines have been established based on this classification (Jaffe, E. S. et al., 2004; see Tables 2 and 3 hereinafter).

Chronic Lymphocytic Leukemia (CLL) is a form of lymphocytic leukemia characterized by slow but progressive accumulation of lymphocytes in the bone marrow and blood. Depending on the stage of the disease, lymph node and spleen enlargement occur commonly. Although CLL may be of T cell or B cell origin, over 85% of the cases are of B-cell origin. Current understanding suggests that CLL is a heterogeneous disease originating from B lymphocytes that differ in their activation and maturation states and cellular subgroup (see Kuppers, R., 2005). The disease may result both from decreased apoptosis as well as increased proliferation of the leukemic B cells. CLL cells are usually clonal in origin, and express the following cell surface markers: CD19, CD20, CD21, and CD24. In addition, they express CD5 which is more typically found on T cells (see Chiorazzi, N, et al. 2005) CLL is considered a subgroup of "non-Hodgkin's lymphoma" (NHL) and together with the closely related disease "small lymphocytic lymphoma" (SLL) which presents primarily in the lymph nodes, corresponds to around 20% of all NHL cases.

CLL is the most common leukemia in adults in the US and most of Western Europe. The National Cancer Institute (NCI) estimate for the incidence of CLL is about 10,000 new cases in the US per year. Clinical manifestations of CLL occur predominantly after the age of 55. The incidence rate for men is higher than for women, with men almost twice as likely to acquire the disease as women.

CLL represents an unmet medical need as there are limited options for treatment.

The most common treatments for NHL are chemotherapy, in particular a combination regimen called CHOP (for Cytoxan, Hydroxyrubicin [Adriamycin], Oncovin [Vincristine], Prednisone), and radiation therapy. In some cases, surgery and bone marrow transplantation have also been used. More recently, there has been an increase in the use of biopharmaceutical agents, especially monoclonal antibodies, such as rituximab and alemtuzumab. Other combination approaches include the use of biopharmaceuticals such as rituximab with chemotherapy. Although these treatments have significantly improved the management of B-lymphoid malignancies, among their deficiencies include non-responsiveness of many patients to these regimens (some patients become refractory to some or all these approaches), and the side effects and complications which result from the use of these treatments. Among the most common side effects of chemotherapy are nausea and vomiting (which is generally managed with the use of antiemetics), alopecia (which is generally reversed over time after completion of treatment), and leukopenia, especially neutropenia. Neutropenia generally develops in the second week. During this period, many clinicians recommend prophylactic use of ciprofloxacin. If a fever develops in the neutropenic period, urgent medical assessment is required for neutropenic sepsis, as infections in patients with low neutrophil counts may progress rapidly. With respect to rituximab, first infusion reaction, lymphopenia, infectious complications such as viral reactivation including Hepatitis B and Progressive Multifocal Leukoencephalopathy (PML), mucocutaneous reactions, and renal complications have been reported. In the case of alemtuzumab, serious hematologic toxicities can occur, including pancytopenia, bone marrow hypoplasia, autoimmune idiopathic thrombocytopenia, and autoimmune hemolytic anemia. In some cases, these toxicities can accelerate morbidity and mortality rates.

SUMMARY OF THE INVENTION

The invention relates to a method of treatment of hematologic malignancies comprising the step of administering to a subject in need thereof a therapeutically effective amount of a ligand of PD1, wherein said ligand of PD1 is selected from the group consisting of PD-L1 or a fragment thereof which binds to PD1, PD-L2 or a fragment thereof which binds to PD1, and an anti-PD1 antibody or a fragment thereof which binds to PD1, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

The invention relates to a ligand of PD1 for the treatment of a hematologic malignancy, wherein said ligand of PD1 is selected from the group consisting of PD-L1 or a fragment thereof which binds to PD1, PD-L2 or a fragment thereof which binds to PD1, and an anti-PD1 antibody or a fragment thereof which binds to PD1, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

The invention relates to an anti-PD1 antibody or a fragment thereof which binds to PD1, wherein said antibody or said fragment induces death and/or elimination of B-cells expressing PD1.

The invention also relates to a method for diagnosing a hematologic malignancy selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma comprising the step of measuring the expression of PD1 in B-cells.

DEFINITIONS

As used herein, references to specific proteins (e.g., antibodies or PD1) can include a polypeptide having a native amino acid sequence, as well as variants and modified forms regardless of their origin or mode of preparation. A protein that has a native amino acid sequence is a protein having the same amino acid sequence as obtained from nature (e.g., a naturally occurring PD1). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

The term "PD1" (The programmed death-1 receptor), as used herein, is intended to designate a type I transmembrane protein, belonging to the CD28-B7 signalling family of receptors that includes CD28, cytotoxic T-lymphocyte-associated antigen 4 (CTLA-4), inducible costimulator (ICOS), and B- and T-lymphocyte attenuator (BTLA) (Greenwald R J et al., 2005, Riley J L et al., 2005).

By "ligand" is meant a natural or synthetic compound which binds to a receptor molecule to form a receptor-ligand complex.

So far, two ligands of PD1 have been identified: PD-L1 (B7-H1) and PD-L2 (B7-DC). PD-L1 and PD-L2 have been characterized as type I transmembrane proteins triggering the PD1 inhibiting effect (Keir M E et al., 2005). Following T-cell activation, expression of PD1 is induced, and engagement with its ligands prevents excessive activation of the immune system (Brown J A et al, 2003). This physiological process is also implicated in the mechanism of peripheral tolerance (Keir M E et al, 2006). Dysfunction of the PD1/PD-L1 pathway is involved in the pathogenesis of various immunological disorders including autoimmunity (Okazaki T et al., 2005), and immunodeficient conditions associated with chronic viral infections (Barber D L et al., 2006, Freeman G J et al., 2006).

In natural antibodies, the two heavy chains are linked to each other by disulfide bonds and each heavy chain is linked to a light chain by a disulfide bond. There are two types of light chains, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin consisting of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs. The term "antibody" is further intended to encompass antibodies, digestion fragments, specified portions and variants thereof, including antibody mimetics or portions of antibodies that mimic the structure and/or function of an antibody or specified fragment or portion thereof, including single chain antibodies and fragments thereof. Functional fragments include antigen-binding fragments that bind to a mammalian PD1.

As used herein, the term "human antibody" refers to an antibody in which a substantial portion of the antibody molecule resembles, in amino acid sequence or structure, that of an antibody derived from human origin. The term "humanized antibody" refers to an antibody which has been modified by genetic engineering or by other means to be similar in structure or amino acid sequence to naturally occurring human antibodies. A "human antibody" or a "humanized antibody" may be considered more suitable in instances where it is desirable to reduce the immunogenicity of the antibody for administration to humans for therapeutic, prophylactic or diagnostic purposes.

A "monoclonal antibody" or "mAb" in its various names refers to a population of antibody molecules that contains only one species of antibody combining site capable of immunoreacting with a particular epitope. A monoclonal antibody thus typically displays a single binding affinity for any epitope with which it immunoreacts. Monoclonal antibody may also define an antibody molecule which has a plurality of antibody combining sites, each immunospecific for a different epitope. For example, a bispecific antibody would have two antigen binding sites, each recognizing a different interacting molecule, or a different epitope. As used herein, the terms "antibody fragment", "antibody portion", "antibody variant" and the like include any protein or polypeptide containing molecule that comprises at least a portion of an immunoglobulin molecule such as to permit specific interaction between said molecule and an antigen (e.g. PD1). The portion of an immunoglobulin molecule may include, but is not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of a ligand or counter-receptor (e.g. PD1) which can be incorporated into an antibody of the present invention to permit interaction with the antigen (e.g. PD1).

The term "hybridoma" denotes a cell, which is obtained by subjecting a B cell, prepared by immunizing a non-human mammal with an antigen, to cell fusion with a myeloma cell derived from a mouse or the like which produces a desired monoclonal antibody having an antigen specificity.

As used herein, the term "subject" denotes a mammal, such as a rodent, a feline, a canine, and a primate. Preferably a subject according to the invention is a human.

DETAILED DESCRIPTION OF THE INVENTION

Therapeutic Methods and Uses

An aspect of the invention relates to a method of treatment of hematologic malignancies comprising the step of administering to a subject in need thereof a therapeutically effective amount of a ligand of PD1, wherein said ligand of PD1 is selected from the group consisting of PD-L1 or a fragment thereof which binds to PD1, PD-L2 or a fragment thereof which binds to PD1, and an anti-PD1 antibody or a fragment thereof which binds to PD1, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

The invention relates to a ligand of PD1 for the treatment of a hematologic malignancy, wherein said ligand of PD1 is selected from the group consisting of PD-L1 or a fragment thereof which binds to PD1, PD-L2 or a fragment thereof which binds to PD1, and an anti-PD1 antibody or a fragment thereof which binds to PD1, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

The invention also relates to the use of a ligand of PD1 for the manufacture of a medicament for the treatment of a hematologic malignancy, wherein said ligand of PD1 is selected from the group consisting of PD-L1 or a fragment thereof which binds to PD1, PD-L2 or a fragment thereof which binds to PD1, and an anti-PD1 antibody or a fragment thereof which binds to PD1, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

In a preferred embodiment the hematologic malignancy is a chronic lymphocytic leukemia of B-cell origin or a small lymphocytic lymphoma of B-cell origin.

Typically said ligand of PD1 may be used in combination with radiotherapy and/or hormone therapy.

Typically said ligand of PD1 may also be used in combination with one or more agents selected from the group consisting of an anticancer agent, an antiemetic agent, an hematopoietic colony stimulating factor, an analgesic agent and an anxiolytic agent.

In a preferred embodiment of the invention, said ligand of PD1 is PD-L1 or PD-L2 or a fragment of PD-L1 or PD-L2 which binds to PD1. Various studies have provided evidence for direct inhibitory effects of the ligands of PD1 PD-L1 and PD-L2 in addition to anti-PD1 antibodies (Freeman et al., 2000; Dong et al., 1999; Latchman et al., 2001; Cai et al., 2004). Anti-CD3 mAb plus either PD-L1-Ig or PD-L2-Ig proteins linked to beads inhibited T cell proliferation and cytokine production by resting or previously activated CD4+ and CD8+ T cells, or naive T cells from cord blood. Inhibition was not seen when T cells lacking PD-1 (i.e. PD-1-/- cells) were incubated with anti-CD3 plus PD-L1-Ig, indicating that the inhibitory signal was transduced via the PD-1 receptor. Studies using Chinese hamster ovary (CHO) cells transfected with MHC class II and PD-L1 or PD-L2, in the presence or absence of B7-2 also support a direct inhibitory role for PD-L1 and PD-L2. The ligands of PD1 exert these effects by causing cell cycle arrest in G0/G1 but not cell death. Engagement of PD1 can also inhibit B cell cycle progression. These studies demonstrate overlapping functions of the PD1 ligands PD-L1 and PD-L2 in inhibiting T cell-dependent immune responses.

In another preferred embodiment, said ligand of PD1 is an anti-PD1 antibody or a fragment thereof which binds to PD1.

Said ligand may induce death and/or elimination of a B-cell expressing PD1, chronic lymphocytic leukemia B-cells and/or small lymphocytic lymphoma (SLL) B-cells in particular, by mechanisms such as antibody-dependent cellular cytotoxicity, complement-mediated cytotoxicity, or recruitment and/or activation of immune effector cells through the production of cytokines and/or chemokines. Indeed, PD1 is involved in cell death by multiple mechanisms that have been demonstrated using mAbs. Signalling via PD1 can play an indirect role via downregulation of growth factor production. It also inhibits expression of the cell survival gene bcl-xL. PD1 signalling also limits glucose metabolism and Akt activation, although via different mechanisms. PD1 signalling blocks CD28-mediated activation of PI3K. Finally PD1 expressing cells are more prone to Fas mediated apoptosis (Chemnitz et al., 2004; Carter et al., 2002).

In a preferred embodiment said anti-PD1 antibody is a monoclonal antibody obtainable from a hybridoma deposited at the COLLECTION NATIONALE DE CULTURES DE MICROORGANISMES (CNCM) located at INSTITUT PASTEUR, 25 rue du Docteur Roux, F-75724, PARIS Cedex 26, France, on Apr. 12, 2007 in accordance with the terms of the Budapest Treaty under the accession number CNCM I-3745.

In a preferred embodiment said ligand of PD1 is an antibody or a fragment thereof which displays the same antigen combining sites as an antibody obtainable by the hybridoma deposited at the CNCM under the number CNCM I-3745.

Such antibodies or fragments can be obtained, for example, by methods used for generating humanized scFv fragments. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see e.g. WO98/45322; WO 87/02671; U.S. Pat. No. 5,859,205; U.S. Pat. No. 5,585,089; U.S. Pat. No. 4,816,567; EP0173494).

In a further embodiment, the invention relates to hybridoma cell line suitable for obtaining anti-PD1 monoclonal antibodies which induce death and/or elimination of a B-cell expressing PD1.

In a preferred embodiment the invention relates to a hybridoma deposited at the COLLECTION NATIONALE DE CULTURES DE MICROORGANISMES (CNCM) under the number CNCM I-3745.

Whereas polyclonal antibodies may be used, monoclonal antibodies are preferred.

Antibodies capable of specific binding to PD1 may be derived from a number of species including, but not limited to, rodent (mouse, rat, rabbit, guinea pig, hamster, and the like), porcine, bovine, equine or primate and the like. Antibodies from primate (monkey, baboon, chimpanzee, etc.) origin have the highest degree of similarity to human sequences and are therefore expected to be less immunogenic. Antibodies derived from various species can be "humanized" by modifying the amino acid sequences of the antibodies while retaining their ability to bind the desired antigen. Antibodies may also be derived from transgenic animals, including mice, which have been genetically modified with the human immunoglobulin locus to express human antibodies. Procedures for raising "polyclonal antibodies" are well known in the art. For example, polyclonal antibodies can be obtained from serum of an animal immunized against PD1, which may be produced by genetic engineering for example according to standard methods well-known by one skilled in the art. Typically, such antibodies can be raised by administering PD1 protein subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times at six weeks' interval. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988).

Although historically monoclonal antibodies were produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988). Monoclonal antibodies (mAbs) may be prepared by immunizing a mammal such as mouse, rat, primate and the like, with purified PD1 protein or a fragment thereof. The antibody-producing cells from the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975). Alternatively, the immunoglobulin genes may be isolated and used to prepare a library for screening for reactive specifically reactive antibodies. Many such techniques including recombinant phage and other expression libraries are known to one skilled in the art.

While mAbs can be produced by hybridoma culture the invention is not to be so limited. Also contemplated is the use of mAbs produced by cloning and transferring the nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

In a particular embodiment, mAbs recognizing PD1 may be generated by immunization of Balb-c mice with the respective recombinant human Fc-IgG1 fusion proteins. Spleen cells were fused with X-63 myeloma cells and cloned according to already described procedures (Olive D, 1986). Hybridoma supernatants were then screened by staining of transfected cells and for lack of reactivity with untransfected cells.

Antibody generation techniques not involving immunisation are also contemplated such as for example using phage display technology to examine naive libraries (from non-immunised animals) (see Barbas et al., 1992, and Waterhouse et al. 1993).

Antibodies of the invention are suitably separated from the culture medium by conventional immunoglobulin purification procedures such as, for example, affinity, ion exchange and/or size exclusion chromatography, and the like.

In a particular embodiment, the antibody of the invention may be a human chimeric antibody. Said human chimeric antibody of the present invention can be produced by obtaining nucleic acid sequences encoding VL and VH domains, constructing a human chimeric antibody expression vector by inserting them into an expression vector for animal cell having genes encoding human antibody CH and human antibody CL, and expressing the expression vector by introducing it into an animal cell. The CH domain of a human chimeric antibody may be any region which belongs to human immunoglobulin, but those of IgG class are suitable and any one of subclasses belonging to IgG class, such as IgG1, IgG2, IgG3 and IgG4, can also be used. Also, the CL of a human chimeric antibody may be any region which belongs to Ig, and those of kappa class or lambda class can be used. Methods for producing chimeric antibodies involve conventional recombinant DNA and gene transfection techniques are well known in the art (see Morrison S L. et al., 1984 and patent documents U.S. Pat. No. 5,202,238; and U.S. Pat. No. 5,204,244).

In another particular embodiment, said antibody may be a humanized antibody. Said humanized antibody may be produced by obtaining nucleic acid sequences encoding for CDRs domain by inserting them into an expression vector for animal cell having genes encoding a heavy chain constant region identical to that of a human antibody; and a light chain constant region identical to that of a human antibody, and expressing the expression vector by introducing it into an animal cell.

The humanized antibody expression vector may be either of a type in which a gene encoding an antibody heavy chain and a gene encoding an antibody light chain exist on separate vectors or of a type in which both genes exist on the same vector (tandem type). In respect of easiness of construction of a humanized antibody expression vector, easiness of introduction into animal cells, and balance between the expression levels of antibody H and L chains in animal cells, a tandem type of the humanized antibody expression vector is more preferable (Shitara K et al. 1994). Examples of the tandem type humanized antibody expression vector include pKAN-TEX93 (WO 97/10354), pEE18 and the like. Methods for producing humanized antibodies based on conventional recombinant DNA and gene transfection techniques are well known in the art (see, e.g. Riechmann L. et al. 1988; Neuberger M S. et al. 1984). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

For example, antibody fragments capable of binding to PD1 or portions thereof, including, but not limited to Fab (e.g., by papain digestion), Fab' (e.g., by pepsin digestion and partial reduction) and F(ab')$_2$ (e.g., by pepsin digestion), Facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention.

Such fragments may be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Said Fab fragment of the present invention can be obtained by treating an antibody which specifically reacts with human PD1 with a protease, papaine. Also, the Fab may be produced by inserting DNA encoding Fab of the antibody into a vector for prokaryotic expression system or for eukaryotic expression system, and introducing the vector into a procaryote or eucaryote to express the Fab.

Said F(ab')$_2$ of the present invention may be obtained by treating an antibody which specifically reacts with PD1 with a protease, pepsin. Also, the F(ab')$_2$ can be produced by binding Fab' described below via a thioether bond or a disulfide bond.

Said Fab' may be obtained by treating F(ab')$_2$ which specifically reacts with PD1 with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote to effect its expression.

Said scFv fragment may be produced by obtaining cDNA encoding the $V_H$ and $V_L$ domains as previously described, constructing DNA encoding scFv, inserting the DNA into an expression vector for prokaryote or an expression vector for eukaryote, and then introducing the expression vector into a prokaryote or eukaryote to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

In a particular embodiment, monoclonal antibodies of the invention are monovalent, bivalent, multivalent, monospecific, bispecific, or multispecific. In another preferred embodiment, the antibody to PD1 is a binding fragment or a conjugate. For examples antibodies of the invention may be conjugated to a growth inhibitory agent, cytotoxic agent, or a prodrug-activating enzyme.

It may be also desirable to modify the antibody of the invention with respect to effector functions, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992).

In addition to receptor-mediated direct effects of targeting via the PD1 receptor, use of anti-PD1 mAbs will facilitate cell death via the Fc portion of the mAb. The role of Fc-effector functions in antibody-dependent processes has been extensively studied in vitro, in vivo in animal models, and in human clinical trials. Targeting antibodies to the tumor results in the destruction of the tumor cells by antibody-dependent cellular cytotoxicity (ADCC) or complement-dependent cytotoxicity (CDC). Another approach to killing the targeted cells is by conjugation of cytotoxic drugs, toxins or radionucleotides to the antibodies.

Use of antibody Fc-effector functions for killing of tumor cells in vivo, which is well known to anyone skilled in the art (see recent review by X. Y. Liu et. al., 2008), forms the basis of many highly successful drugs in current clinical use including rituximab, trastuzumab, gemtuzumab and alemtuzumab, and many others in advanced clinical development. In addition to facilitating Fc-effector functions such as ADCC and CDC, mAbs have also been successfully used to deliver to tissues and cells such agents as toxins, radionuclides and cytotoxic drugs; examples include ibritumomab tiuxetan, tositumomab and pemtumomab.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojar H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non-proteinaceous polymers, e.g. polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337.

A further object of the invention relates to a method of treating hematologic malignancies comprising administering in a subject in need thereof a therapeutically effective amount of ligand of PD1 as defined above, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of such a disorder or condition.

By a "therapeutically effective amount" of the ligand of PD1 according to the invention is meant a sufficient amount of the ligand of PD1 to treat said hematologic malignancy, at a reasonable benefit/risk ratio applicable to any medical treatment. It will be understood, however, that the total daily usage of the ligand of PD1 and compositions of the present invention will be decided by the attending physician within the scope of sound medical judgment. The specific therapeutically effective dose level for any particular patient will depend upon a variety of factors including the disorder being treated and the severity of the disorder, activity of the specific ligand of PD1 employed; the specific composition employed, the age, body weight, general health, sex and diet of the patient, the time of administration, route of administration, and rate of excretion of the specific antibody employed, the duration of the treatment; drugs used in combination or coincidental with the specific polypeptide employed, and like factors well known in the medical arts. For example, it is well known within the skill of the art to start doses of the compound at levels lower than those required to achieve the desired therapeutic effect and to gradually increase the dosage until the desired effect is achieved.

Ligands of PD1 according to the invention may be used in combination with any other therapeutic strategy for treating the disorders or conditions as above described (e.g. external radiotherapy, chemotherapy or hormone therapy or cytokine therapy).

Pharmaceutical Compositions

A further object of the invention relates to a pharmaceutical composition comprising an effective dose of a ligand of PD1.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of a ligand of PD1 may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

A ligand of PD1 of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

Compositions of the present invention may comprise a further therapeutic active agent. The present invention also relates to a kit comprising a ligand of PD1 as defined above and a further therapeutic active agent.

In one embodiment said therapeutic active agent is an anticancer agent. For example, said anticancer agents include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycins, anthracyclines, MDR inhibitors and $Ca^{2+}$ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or muti-specific antibodies, monobodies, polybodies.

Additional anticancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a preferred embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the further therapeutic active agent can be an opioid or non-opioid analgesic agent Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

Screening Methods

Fragments of anti-PD1, PD-L1 or PD-L2 which bind to PD1 may be selected by any screening methods well known in the art.

For example, a method for the in vitro screening of ligands of PD1 may comprise the following steps:
(a) adding fragments of anti-PD1, PD-L1 or PD-L2 to B-cells expressing PD1;
(b) selecting the fragments which bind to the cells.

Diagnostic Methods and Uses

An aspect of the invention relates to the use of an anti-PD1 antibody or a fragment thereof which binds to PD1 for the detection of a B cell selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

The invention also relates to the use of an anti-PD1 antibody or a fragment thereof which binds to PD1 for diagnosing in a subject a hematologic malignancy selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

PD1 may be used as a marker of a hematologic malignancy selected the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma.

The invention also relates to a method for diagnosing in a subject a hematologic malignancy selected from the the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma, comprising the step of measuring the expression of PD1 in B-cells obtained from said subject.

Typically methods and uses according to the invention may not be practised on the human or animal body.

Typically methods and uses according to the invention may be performed ex vivo or in vitro.

Typically anti-PD1 antibodies or fragments thereof which bind to PD1 may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the probe or antibody by reactivity with a detectable substance.

An anti-PD1 antibody or a fragment thereof which binds to PD1 may be labelled with a radioactive molecule by any method known to the art. For example radioactive molecules include but are not limited radioactive atom for scintigraphic studies such as $I^{123}$, $I^{124}$, $In^{111}$, $Re^{186}$, $Re^{188}$.

Said antibody or fragment thereof may also be labelled with a spin label for nuclear magnetic resonance (NMR) imaging (also known as magnetic resonance imaging, MRI), such as iodine-123, iodine-131, indium-III, fluorine-19, carbon-13, nitrogen-15, oxygen-17, gadolinium, manganese or iron.

Anti-PD1 antibody or a fragment thereof which binds to PD1 may be useful for staging of a hematologic malignancy selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma, CLL or SLL in particular, (e.g., in radioimaging). They may be used alone or in combination with other markers of the hematologic malignancy.

The term "detection" as used herein includes qualitative and/or quantitative detection (measuring levels) with or without reference to a control.

The invention will be further illustrated through the following examples, figures and tables.

FIGURES

FIG. 1: Flow cytometry analysis of PD1 expression in B-SLL and B-CLL cells. Panel A shows PD1 basal expression in blood cells from 3 CLL samples (CLL-1, CLL-2 and CLL-3), with mean fluorescence intensities (MFI) ranging from 159 to 223 (negative controls ranged from 65 to 72). Panel B shows PD1 expression in SLL cells teased from a lymph node sample. In unstimulated SLL cells (left), the expression was higher than in CLL cells (MFI for PD1 and for negative control were 1050 and 210, respectively). In activated cells (right), the level of expression was not modified by either CD32 or CD40 stimulation. Panel C shows enhancement of PD1 expression in blood cells from 2 CLL cases (CLL-4 and CLL-5) by CD40 stimulation. The negative controls corresponded to CD32 activation and to replacement of PD1 MAb by IgG2B (left). As regards CLL-4, MFI for CD32 and CD40 activation were 264 and 478, respectively. As regards CLL-5, MFI for CD32 and CD40 activation were 206 and 441, respectively.

TABLES

TABLE 1

Summary of immunohistochemical and flow cytometry analysis of PD1 expression in Lymphoid neoplasms.

| | Samples | PD1 positivity of neoplastic cells |
|---|---|---|
| B-cell lymphomas | B-SLL | 9/10 (++ to +++)* |
| | B-CLL** | 10/11 |
| | Diffuse Large Cell | 2/25 (+)* |
| | Follicular | 3/43 (+)* |
| | Mantle zone | 0/5 |
| | Marginal zone | 0/4 |
| | Burkitt | 0/3 |
| T-cell lymphomas | Angioimmunoblastic | 5/5 (+++)* |
| | Anaplastic | 0/1 |
| | Unspecified | 0/2 |
| | Lymphoblastic | 0/3 |
| Hodgkin's lymphomas | Classical | 0/30 |
| | Lymphocyte predominance | 0/5 |

*Refers to the proportion of positive cells, as described in the Material and Methods section.
**Blood CLL B-cells were analyzed by flow cytometry, whereas all other cases were lymph node tumours analysed by IHC.

TABLE 2

WHO classification of B-cell lymphoid neoplasms
(Jaffe, E. S. et al., 2004).

Precursor B-cell neoplasm

Precursor B-lymphoblastic leukemia/lymphoma
Mature B-cell neoplasms

Chronic lymphocytic leukemia/small lymphocytic lymphoma
Variant: with plasmacytoid differentiation or monoclonal gammopathy
B-cell prolymphocytic leukemia
Lymphoplasmacytic lymphoma
Splenic marginal zone B-cell lymphoma (± villous lymphocytes)
Hairy cell leukemia
Variant: hairy cell variant
Plasma cell myeloma/plasmacytoma
Extranodal marginal zone B-cell lymphoma of MALT type
Nodal marginal zone B-cell lymphoma (± monocytoid B cells)
Follicular lymphoma
Variants:

Cutaneous follicle center lymphoma
Diffuse follicle center lymphoma
Mantle cell lymphoma
Variant: blastoid
Diffuse large B-cell lymphoma
Subtypes:

Mediastinal large B-cell lymphoma
Intravascular large B-cell lymphoma
Primary effusion lymphoma
Morphologic variants
Centroblastic
Immunoblastic
Anaplastic large B-cell
T-cell/histiocyte-rich
Plasmablastic
Lymphomatoid granulomatosis-type
Burkitt's lymphoma/Burkitt's cell leukemia
Morphologic variants
Classical
Atypical
With plasmacytoid differentiation (AIDS-associated)
Subtypes (clinical and genetic)
Endemic
Sporadic
Immunodeficiency-associated
B-cell proliferations of uncertain malignant potential Lymphomatoid granulomatosis (grades 1, 2 and 3)
Post-transplant lymphoproliferative disease

TABLE 3

WHO classification of T-cell and NK-cell lymphoid neoplasms
(Jaffe, E. S. et al., 2004).

Precursor T-cell neoplasm

Precursor T-lymphoblastic lymphoma/leukemia
Mature (peripheral) T-cell and NK-cell neoplasms T-cell prolymphocytic leukemia
Morphologic variants: small cell, cerebriform cell
T-cell granular lymphocytic leukemia
Aggressive NK-cell leukemia
Blastic 'NK-cell' lymphoma
Adult T-cell leukemia/lymphoma (HTLV-1+)
Clinical variants Acute
Lymphomatous
Chronic
Smoldering
Hodgkin-like
Extranodal NK/T-cell lymphoma, nasal type
Enteropathy-type T-cell lymphoma

TABLE 3-continued

WHO classification of T-cell and NK-cell lymphoid neoplasms
(Jaffe, E. S. et al., 2004).

Hepatosplenic T-cell lymphoma
Subcutaneous panniculitis-like T-cell lymphoma
Mycosis fungoides/Sezary syndrome
Variants Pagetoid reticulosis
MF-associated follicular mucinosis
Granulomatous slack skin disease
Primary cutaneous CD30+ T-cell lymphoproliferative disorder
Variants Lymphomatoid papulosis (type A and B)
Primary cutaneous anaplastic large-cell lymphoma
Borderline lesions
Peripheral T-cell lymphoma, not otherwise characterized
Morphologic variants: lymphoepithelioid (Lennert's), T-zone
Angioimmunoblastic T-cell lymphoma
Anaplastic large cell lymphoma, (ALK+/ALK−)
Morphologic variants: lymphohistiocytic, small cell

EXAMPLES

Example 1

Materials and Methods

Generation of Anti-PD1, -PD-L1 and -PD-L2 MAbs

MAbs recognizing PD1 (clones PD1-6-4, obtainable from hybridoma CNCM I-3745, and PD1-3-1), PD-L1 (clone PD-L1-3) and PD-L2 (clone PD-L2-1) were generated by immunization of balb-c mice with the respective recombinant human Fc-IgG1 fusion proteins. Spleen cells were fused with X-63 myeloma cells and cloned according to already described procedures [Olive et al. 1986]. Hybridoma supernatants were screened by staining of transfected cells and for lack of reactivity with untransfected cells. The PD1-6-4 clone (mouse IgG1) was chosen for further IHC analysis based on its capacity to stain paraffin embedded tissues, whereas the PD1-3-1 clone was used for FC analysis due to a better sensitivity. PD-L1-3 and PD-L2-1 MAbs could be used only on frozen sections.

Tissue Sampling

A total of 136 lymphoma biopsy samples from patients with informed consent was analyzed, including 35 cases of HL and 101 specimens of NHLs. Low and high grade B-cell NHLs [n=90], and T-cell NHLs [n=11] were classified according to the WHO classification [Jaffe et al., 2001]. HL subtypes were classified as lymphocyte predominance (n=5) nodular sclerosing [n=22] and mixed cellularity [n=8]. Diagnosis was based on conventional morphological examination of paraffin embedded material. When required, diagnoses were refined by IHC using MAbs recognizing B-cells, T-cells, or Reed-Sternberg cells (RSC). Fresh tissues could also be obtained and were stored at −70° C. until use. A control group of non neoplastic tissues from reactive lymphadenitis [n=7] was also tested.

Immunohistochemistry (IHC)

Single IHC Stainings.

PD1 immunostaining was performed on either total paraffin sections or on tissue microarrays (TMA), which were constructed as previously described [Ballester et al. 2006] using 1 mm cores of each paraffin-embedded tumour and a manual tissue arrayer (Beecher Instruments, Sun Prairie, Wis., USA). Five μm-thick sections were submitted to microwave antigen retrieval in 10 mM S199 buffer, pH 9.0. Results were analysed using a Spot Browser™ automated image analysis system (Alphelys, Plaisir, France). Positive controls were sections of reactive lymph nodes, which are known to contain variable numbers of PD1 positive T-cells [Dorfman et al. 2006]. Negative controls were performed by omitting the primary mAb.

Immunostaining for PD1 ligand and PD-2 ligands was performed using the PD-L1-3-1 and PD-L2-1 MAbs on frozen sections from neoplastic and reactive lymph nodes as previously described [Xerri et al. 1997]. Immunostaining in a given cell population was evaluated as negative (0) if less than 1% of the cells were positive, positive, +, if 1 to 50% of the cells were positive, ++, if 50 to 75% of the cells were positive, and +++, if greater than 75% of the cells were positive.

Double and Serial IHC Stainings

For double and serial IHC stainings, we selected a panel of MAbs directed against different lymphocyte subsets: CD3 for T-cells, PAX5 for B-cells, FOXP3 for Treg cells, CXCL13 for T-Fh cells and CD23 for FDC cells. MAbs for CD3, CD23 and PAX5 were from DakoCytomation (DakoCytomation, Glosturp, Denmark); antibodies for CXCL13 and FOXP3 were from R&D systems (Lille, France) and from eBioscience (San Diego Calif., USA), respectively.

Sections from a group of selected PD1-positive tissues were double stained for PD1, and for either PAX5, FOXP3 or CD3, respectively. Detection of the first antigen was performed by a three stage mouse peroxydase anti-peroxydase technique, and detection of PAX5, FOXP3 or CD3 was by the APAAP procedure using the DAKO kit according to the supplier recommendation. Anti-CXCL13 and -CD23 MAbs were used on serial sections alternatively stained for PD1.

Flow Cytometry (FC) Analysis of PD1 Expression

Fresh blood CLL cells were collected from 11 patients with informed consent. Ficoll separated mononuclear cells were washed, and resuspended in RPMI medium containing 10% fetal calf serum (FCS). For FC analysis of PD1 expression, lymphoma cells were incubated with an Alexa-647 conjugated anti-PD1 MAb (clone PD1-3-1) for 30 min at 4° C. Cells were then washed in phosphate-buffered saline (PBS), fixed with 1% paraformaldehyde and analyzed on a FACS-Canto flow cytometer (Becton Dickinson, San Jose, Calif., USA). An Alexa-647-conjugated mouse IgG2b was used as isotypic control. Positive controls for PD1 expression were PBL cells activated with PHA (10 mg/ml) for 24 hours. Non-activated cells were used as a negative control.

CD40 Activation Functional Analysis

The influence of CD40 activation on PD1 expression was analyzed in blood cells from 11 CLL cases, and lymph node cells from 1 SLL case. Fresh blood CLL cells and SLL cells obtained by immediate teasing of a surgically removed lymph node were washed and resuspended in RPMI medium containing 20% FCS. Isolated B-cells were uniformly >90% CD20+ and <10% CD3+. They were analyzed for PD1 expression using FC and then submitted to CD40L-triggering as described previously [18]. Briefly, L cells stably expressing the human CD40 ligand (CD40L) were seeded at $1\times10^5$ cells/ml as a feeder layer before adding the malignant lymphoma cells. B-cells were submitted to CD40 stimulation for 48 h and then analyzed again for PD1 expression.

Results

Characterization of the Monoclonal Anti-PD1 Antibody PD1-6-4

The analysis of the expression of molecules in tissues relies on their ability to be detected by mAbs followed by detection by histochemistry or immunofluorescence. However, the best current tissue fixations impair in most instances the ability of Mab to detect efficiently their epitope on their specific antigen. Few mabs are able to keep their ability to stain their antigen even in IHC on the more efficient protocol ie formalin-fixed, paraffin-embedded tissue sections.

Notably, the inventors have demonstrated that the monoclonal anti-PD1 antibody PD1-6-4, obtainable from hybridoma CNCM I-3745, keeps its ability to stain efficiently PD1 molecules in various paraffin-embedded tumor samples. This antibody therefore has important advantages over currently available reagents, particularly in use for diagnosis.

PD1 is Mainly Expressed in Follicular T Cells in Reactive Lymph Nodes

In samples of lymph node displaying non specific reactive features, including follicular hyperplasia, PD1 immunostaining was mainly observed in small lymphocytes scattered within the germinal centers, which were often polarized to the light zone, or arranged in small linear clusters close to the mantle zone, Only rare positive cells were found in the interfollicular T-cell areas. Using dual PD1/FOXP3 staining, these interfollicular PD1 positive cells exhibited no significant FOXP3 staining. PD1 positivity was mostly localized at the cell surface, but cytoplasmic signals were occasionally observed as golgian dots.

When compared to PD1 stained sections, serial sections stained with either CD3 or CXCL13 exhibited an almost similar pattern of positivity within the GC. Dual color CD3/PD1 immunostaining confirmed that, within the GC, virtually all CD3 positive T-cells were PD1-positive cells. The combined PAX5/PD1 immunostaining showed no PD1 staining on PAX5 positive B-cells in most cases. However, in one case of reactive lymphadenitis displaying particularly bulky germinal centers, we could observe a weak PD1 staining in rare GC large centroblastic B-cells.

PD1 is Expressed in Reactive T-Cells from Most NHLs and HL Tissues

PD1 positivity was detected in variable amounts of reactive small T-cells from most B-NHL and HL cases, including classical HL and lymphocyte-predominant HL. RSC and variants were negative. Rosetting of PD1 positive cells around CD20-positive neoplastic cells was constantly observed in the lymphocyte-predominant HL subtype.

PD1 was expressed in neoplastic T-cells from angioimmunoblastic T-NHL, but not in other T-NHL subtypes.

Results of the immunohistochemical analysis of lymphoid tumors are summarized in Table 1. Among the 11 T-NHL samples, only the 5 AIL cases displayed PD1-positivity of neoplastic cells, which were identified as T-cells by dual staining using CD3. In contrast, samples from other T-NHL subtypes, including anaplastic large cell lymphoma, "unspecified" peripheral T-NHL and lymphoblastic T-NHL showed no PD1 positivity on neoplastic cells. In AIL tissues, PD1-positive cells represented about 30% to 50% of the total cell population, and were predominantly localized in close vicinity of aggregates of CD23+follicular dendritic cells (FDCs), as shown by stainings of serial sections.

PD1 was expressed in neoplastic B-cells from most nodal SLL/CLL cases, but only exceptionally in other nodal B-NHL subtypes.

Among nodal B-cell NHLs, small lymphocytic lymphoma (SLL) was the only subtype in which the malignant B-cells exhibited immunohistochemical PD1 positivity in a significant proportion of cases (9/10). The signal intensity was weaker on neoplastic cells than on reactive T-cells within the same tumor tissue. The localization of PD1 expression in the B-cell component was further demonstrated by PD1/PAX5 and PD1/CD3 dual labelling. PD1 immunostaining was not uniform among malignant B-cells. The strongest signals were found in large para-immunoblasts and prolymphocytes located within proliferation centers, whereas small B-cells in the surrounding areas were less strongly positive.

Most other subtypes of B-NHLs exhibited no PD1 positivity among the malignant cell population, including mantle cell lymphoma (MCL; 0/5), marginal zone lymphoma (MZL; 0/4) and burkitt lymphoma (BL; 0/3). As mentioned above, all B-NHLs samples contained a variable proportion of PD1-labeled reactive T-cells. Exceptional cases of diffuse large cell lymphoma (DLCL) (2/25) and follicular lymphomas (FL) (3/43) contained PD1 positive B-cells. Interestingly, the 3 positive FL cases were classified as grade 3, whereas negative FL cases were either grade 1 or 2.

PD1 was expressed in blood cells from chronic lymphocytic leukemia (CLL) patients, and could be upregulated by CD40 stimulation.

FC analysis showed a weak, but significant PD1 positivity in 10/11 CLL cases analyzed (FIG. 1A). When compared with fresh SLL lymphoma cells purified from lymph node and similarly analyzed, the level of expression was clearly higher in SLL cells than in blood CLL cells with a ratio of mean fluorescence intensity PD1/IgG2b (SLL) 5.3 versus 3.2 for CLL (FIG. 1C).

After 2 days growth in the presence of CD40L, the level of expression in SLL cells remained unchanged, whereas a significant increase in PD1 expression was observed in most CLL cells.

Among our CLL cases, there was no correlation between the level of PD1 expression and usual prognostic parameters including ZAP-70 expression, mutations of the heavy chain immunoglobulin gene and deletion of the 17p13.1 chromosome region (data not shown).

PD-L1 and PD-L2 are not Expressed in SLL/CLL Cells.

In samples of reactive lymph node and tonsils, both PD-L1 and PD-L2 MAbs gave a similar pattern of IHC positivity, which was restricted to GC follicular dendritic cells (FDC), rare macrophages and small vessels.

PD-L1 and/or PD-L2 positive cells were rare in small cell B-NHLs including SLL, MCL, MZL and FL. They were identified as macrophages, FDC or endothelial cells. In DLCL samples, PD-L1 and PD-L2 positive cells were more numerous and included reactive lymphocytes, whereas a frequent staining was present on neoplastic cells. In HL cases, PD-L1 constantly stained malignant L&H cells from the lymphocyte-predominant subtype, whereas RSC in classical HD tissues were often positive.

PD1 is Expressed by Other B Cell Malignancies Corresponding to Different Stages of B Cell Differentiation.

We have also found expression of PD1 in other B cell malignancies whether they correspond to B precursors (B-ALL), mature B cells (mantle cell lymphoma) or plasma cells (plasma cell leukemia and multiple myeloma).

REFERENCES

All the references cited are incorporated herein by reference.

Ballester B, Ramuz O, Gisselbrecht C, Doucet G, Loi L, Loriod B, et al. Gene expression profiling identifies molecular subgroups among nodal peripheral T-cell lymphomas. Oncogene 2006; 25:1560-1570.

Barbas C F, Bain J D, Hoekstra D M, Lerner R A. (1992), Semisynthetic combinatorial antibody libraries: a chemical solution to the diversity problem. PNAS USA, 89, 4457-4461.

Barber D L, Wherry E J, Masopust D, Zhu B, Allison J P, Sharpe A H, et al. Restoring function in exhausted CD8 T cells during chronic viral infection. Nature 2006; 439:682-687.

Brown J A, Dorfman D M, Ma F R, Sullivan E L, Munoz O, Wood C R, et al. Blockade of programmed death-1 ligands on dendritic cells enhances T cell activation and cytokine production. J Immunol 2003; 170:1257-1266.

Cai G, Karni A, Oliveira E M, Weiner H L, Hafler D A, Freeman G J. 2004. PD-1 ligands, negative regulators for activation of naive, memory, and recently activated human CD4+ T cells. Cell Immunol. 230:89-98.

Caron P C, Laird W, Co M S, Avdalovic N M, Queen C, Scheinberg D A. Engineered humanized dimeric forms of IgG are more effective antibodies. J Exp Med. 1992 Oct. 1; 176(4):1191-5.

Carter L L, Fouser L A, Jussif J, Fitz L, Deng B, et al. 2002. PD-1:PD-L inhibitory pathway affects both CD4+ and CD8+ T cells and is overcome by IL-2. Eur. J. Immunol. 32:634-43.

Chemnitz J M, Parry R V, Nichols K E, June C H, Riley J L. 2004. SHP-1 and SHP-2 associate with immunoreceptor tyrosine-based switch motif of programmed death 1 upon primary humanT cell stimulation, but only receptor ligation prevents T cell activation. J. Immunol. 173:945-54.

Chiorazzi, N., K. R. Rai, and M. Ferrarini. Chronic lymphocytic leukemia. N Engl J Med, 2005. 352(8): p. 804-15.

Dong H D, Zhu G F, Tamada K, Chen L P. 1999. B7-H1, a third member of the B7 family, co-stimulates T-cell proliferation and interleukin-10 secretion. Nat. Med. 5:1365-69

Dorfman D M, Brown J A, Shahsafaei A, Freeman G J. Programmed death-1 (PD1) is a marker of germinal center-associated T cells and angioimmunoblastic T-cell lymphoma. *Am J Surg Pathol* 2006; 30:802-810.

Edge A S, Faltynek C R, Hof L, Reichert L E Jr, Weber P. Deglycosylation of glycoproteins by trifluoromethanesulfonic acid. Anal Biochem. 1981 Nov. 15; 118(1):131-7.

Freeman G J, Long A J, Iwai Y, Bourque K, Chernova T, et al. 2000. Engagement of the PD-1 immunoinhibitory receptor by a novel B7 family member leads to negative regulation of lymphocyte activation. J. Exp. Med. 192:1027-34.

Freeman G J, Wherry E J, Ahmed R, Sharpe A H. Reinvigorating exhausted HIV-specific T cells via PD-1-PD-1 ligand blockade. J Exp Med 2006; 203:2223-2227.

Freireich, E. J. and N. Lemak. Milestones in Leukemia Research and Therapy. 1991, Baltimore: Johns Hopkins University Press.

Greenwald R J, Freeman G J, Sharpe A H. The B7 family revisited. Annu Rev Immunol 2005; 23:515-548.

Harlow E. et al., Antibodies: A Laboratory Manual, Cold Spring Harbor Laboratory, New York, (1988).

Jaffe E S, Harris N L, Stein H, Vardiman J W, eds. Pathology and Genetics of Tumours of Haematopoietic and Lymphoid Tissues. IARC Press: Lyon, France 2001:189-235.

Jaffe, E. S., P. M. Banks, B. Nathwani, J. Said, and S. H. Swerdlow. Recommendations for the reporting of lymphoid neoplasms: A report from the Association of Directors of Anatomic and Surgical Pathology. Mod Pathol, 2004. 17(1): p. 131-5.

Keir M E, Latchman Y E, Freeman G J, Sharpe A H. Programmed death-1 (PD-1):PD-ligand 1 interactions inhibit TCR-mediated positive selection of thymocytes. J Immunol 2005; 175:7372-7379.

Keir M E, Liang S C, Guleria I, Latchman Y E, Qipo A, Albacker L A, et al. Tissue expression of PD-L1 mediates peripheral T cell tolerance. J Exp Med 2006; 203:883-895.

Kohler and Milstein (1975) Continuous cultures of fused cells secreting antibody of predefined specificity. Nature; 256, 495-7.

Kuppers, R. Mechanisms of B-cell lymphoma pathogenesis. Nat Rev Cancer, 2005. 5(4): p. 251-62.

Latchman Y, Wood C R, Chernova T, Chaudhary D, Borde M, et al. 2001. PDL2 is a second ligand for PD-1 and inhibits T cell activation. Nat. Immunol. 2:261-68.

Liu, X. Y., L. M. Pop, and E. S. Vitetta. 2008. Engineering therapeutic monoclonal antibodies. Immunol Rev 222:9-27.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Neuberger M S, Williams G T, Fox R O. Recombinant antibodies possessing novel effector functions. Nature. 1984 Dec. 13-19; 312(5995):604-8.

Okazaki T, Wang J. PD1/PD-L pathway and autoimmunity. Autoimmunity 2005; 38:353-357.

Olive D., Raymond J., Dubreuil P., Charmot D., Jacques Y., Mawas C. Anti-Interleukin 2 receptor monoclonal antibodies. Respective role of epitope mapping and monoclonal antibody-receptor interactions in their antagonist effects on interleukin 2-dependent T cell growth. Eur J Immunol 1986; 16: 611-616.

Padlan E A. A possible procedure for reducing the immunogenicity of antibody variable domains while preserving their ligand-binding properties. Mol Immunol. 1991 April-May; 28(4-5):489-98.

Riechmann L, Clark M, Waldmann H, Winter G Reshaping human antibodies for therapy. Nature. 1988 Mar. 24; 332 (6162):323-7.

Riley J L, June C H. The CD28 family: a T-cell rheostat for therapeutic control of T-cell activation. Blood 2005; 105: 13-21.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Shopes B. A genetically engineered human IgG mutant with enhanced cytolytic activity. J Immunol. 1992 May 1; 148 (9):2918-22.

Sojar H T, Bahl O P. A chemical method for the deglycosylation of proteins. Arch Biochem Biophys. 1987 Nov. 15; 259(1):52-7.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Thotakura N R, Bahl O P. Enzymatic deglycosylation of glycoproteins. Methods Enzymol. 1987; 138:350-9.

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Xerri L, Devilard E, Hassoun J, Olive D, Birg F. In vivo expression of the CTLA4 inhibitory receptor in malignant and reactive cells from human lymphomas. *J Pathol* 1997; 183:182-187.

The invention claimed is:

1. A method for treating a hematologic malignancy, comprising the administration of a ligand of PD1, wherein said ligand of PD1 is an anti-PD1 monoclonal antibody or an antigen binding fragment thereof which binds to PD1 and induces death and/or elimination of a B-cell expressing PD1, said monoclonal antibody being selected from the group consisting of a monoclonal antibody obtainable from a hybridoma deposited at the COLLECTION NATIONALE DE CULTURES DE MICROORGANISMES (CNCM) as CNCM I-3745 and a monoclonal antibody comprising the three complementary determining regions (CDRs) from each of the heavy and light chain variable regions of the monoclonal antibody obtainable from hybridoma CNCM I-3745, and said antigen binding fragment comprising a sequence of the monoclonal antibody obtainable from hybridoma CNCM I-3745 that comprises at least the three light chain CDRs and the three heavy chain CDRs of the monoclonal antibody, and wherein the hematologic malignancy is selected from the group consisting of a chronic lymphocytic leukemia of B-cell origin and a small lymphocytic lymphoma of B-cell origin.

* * * * *